(12) United States Patent
Hart (10) Patent No.: US 7,169,156 B2
(45) Date of Patent: Jan. 30, 2007

(54) SUTURE GRASPING DEVICE

(75) Inventor: Rickey D. Hart, Plainville, MA (US)

(73) Assignee: Innovasive Devices, Inc., Hopkinton, MA (US)

( * ) Notice: Subject to any disclaimer, the term of this patent is extended or adjusted under 35 U.S.C. 154(b) by 0 days.

(21) Appl. No.: 10/623,884

(22) Filed: Jul. 21, 2003

(65) Prior Publication Data

US 2004/0097976 A1    May 20, 2004

Related U.S. Application Data (63) Continuation of application No. 09/742,023, filed on Dec. 20, 2000, now abandoned, which is a continuation of application No. 09/309,072, filed on May 10, 1999, now abandoned, which is a continuation of application No. 08/851,528, filed on May 5, 1997, now abandoned, which is a continuation of application No. 08/443,093, filed on May 17, 1995, now abandoned, which is a continuation of application No. 08/375,129, filed on Jan. 19, 1995, now abandoned, which is a continuation of application No. 08/097,154, filed on Jul. 26, 1993, now abandoned.

(51) Int. Cl.
*A61B 17/04* (2006.01)

(52) U.S. Cl. .............. 606/144; 606/148; 606/206; 606/207; 112/169

(58) Field of Classification Search .............. 606/140, 606/141, 148, 139, 205, 206, 207, 144; 112/169
See application file for complete search history.

(56) References Cited

U.S. PATENT DOCUMENTS

| | | | |
|---|---|---|---|
| 2,137,710 A | * | 11/1938 | Anderson .................. 606/206 |
| 2,416,260 A | | 2/1947 | Karle |
| 2,541,246 A | | 2/1951 | Held |
| 3,877,434 A | | 4/1975 | Ferguson et al. |
| 3,967,625 A | | 7/1976 | Yoon |
| 3,989,049 A | | 11/1976 | Yoon |
| 4,174,715 A | * | 11/1979 | Hasson .................. 606/206 |
| 4,393,872 A | | 7/1983 | Reznik et al. |
| 4,493,319 A | | 1/1985 | Polk et al. |

(Continued)

FOREIGN PATENT DOCUMENTS

WO    WO 91/02493 A1    3/1991

(Continued)

*Primary Examiner*—Michael Thaler
(74) *Attorney, Agent, or Firm*—Pandiscio & Pandiscio (57) ABSTRACT

A device for snaring cord-like objects is provided. The device comprises a hollow shaft having a pointed distal end, a rod having a pair of wires attached to its distal end, the wires being spring biased away from one another, and activation means. The rod and wires are located in the lumen of the shaft in reciprocally movable relationship therewith. The activation means is attached to the proximal ends of the shaft and the rod so as to allow the controlled movement of the rod and wires relative to the shaft. One of the wire-like elements defines a hook-shaped configuration at its distal end. The device allows the wire-like elements to be selectively located within the distal end of the shaft or in a configuration wherein the wire-like elements extend outwardly from the distal end of the shaft in flaring relationship to one another.

2 Claims, 5 Drawing Sheets

U.S. PATENT DOCUMENTS

| | | |
|---|---|---|
| 4,779,616 A | 10/1988 | Johnson |
| 4,898,155 A | 2/1990 | Ovil et al. |
| 4,901,721 A | 2/1990 | Hakki |
| 4,927,428 A | 5/1990 | Richards |
| 4,957,498 A | 9/1990 | Caspari et al. |
| 4,994,079 A | 2/1991 | Genese et al. |
| 5,026,379 A * | 6/1991 | Yoon .................. 606/141 |
| 5,108,406 A | 4/1992 | Lee |
| 5,209,747 A | 5/1993 | Knoepfler |
| 5,222,973 A | 6/1993 | Sharpe et al. |
| 5,222,977 A | 6/1993 | Esser |
| 5,226,426 A * | 7/1993 | Yoon .................. 600/566 |
| 5,226,908 A | 7/1993 | Yoon |
| 5,318,589 A * | 6/1994 | Lichtman .............. 606/205 |

FOREIGN PATENT DOCUMENTS

| | | |
|---|---|---|
| WO | WO 91/17712 | 11/1991 |

* cited by examiner

SUTURE GRASPING DEVICE

REFERENCE TO PENDING PRIOR PATENT APPLICATION

This is a continuation of prior U.S. patent application Ser. No. 09/742,023 filed Dec. 20, 2000 by Rickey D. Hart for SUTURE GRASPING DEVICE, which is in turn a continuation of application Ser. No. 09/309,072 filed May 10, 1999 by Rickey D. Hart for SUTURE GRASPING DEVICE, which is in turn a continuation of application Ser. No. 08/851,528 filed May 5, 1997 by Rickey D. Hart for SUTURE GRASPING DEVICE, which is in turn a continuation of application Ser. No. 08/443,093 filed May 17, 1995 by Rickey D. Hart for SUTURE GRASPING DEVICE, which is in turn a continuation of application Ser. No. 08/375,129 filed Jan. 19, 1995 by Rickey D. Hart for SUTURE GRASPING DEVICE, which is in turn a continuation of application Ser. No. 08/097,154 filed Jul. 26, 1993 by Rickey D. Hart for SUTURE GRASPING DEVICE all abandoned.

FIELD OF THE INVENTION

The present invention generally relates-to devices for snaring suture or other cord-like material. More particularly, the present invention relates to suture grasping devices suitable for use in drawing suture through tissue, in both open and closed surgical procedures.

BACKGROUND OF THE INVENTION

Devices for grasping free suture ends during surgical procedures are well known in the art. In one such device, an elongate element is provided. This element has a flexible, closed loop at one end. The elongate element is telescopically mounted inside a hollow shaft so that the loop can be alternately withdrawn into, or projected out of, the distal end of the shaft. In use, the device is manipulated so that the distal end of the shaft is brought into the vicinity of the free end of the suture which is to be grasped, the loop is projected out of the distal end of the shaft, the device is further manipulated until the free end of the suture extends through the loop, and then the loop is withdrawn back into the shaft so as to grasp the suture and hold it tight against the distal end of the shaft.

While devices of the type described above work, they also present several drawbacks. For one thing, it is often difficult (or impossible) to access a free end of the suture, even where some intermediate portion of the suture has been located. This is particularly true in closed surgeries, where visibility is frequently quite limited and space at the surgical site relatively restricted. Furthermore, in many surgical procedures, a free suture end needs to be passed through soft tissue before it is grasped and then tied off. In these situation's, needles need to be attached to the free suture ends and then manipulated through the soft tissue using separate surgical instruments before the suture grasping device is employed. The,need to use such multiple instruments in order to effect the desired suture passage and snaring may be inconvenient and cumbersome, particularly in closed surgical settings.

OBJECTS OF THE INVENTION

Accordingly, one object of the present invention is to provide a suture grasping device adapted to easily and conveniently grasp a length of suture at any point along, the suture's length.

Another object of the present invention is to provide a suture grasping device which may be used in both open and closed surgical procedures.

Still another object of the present invention is to provide a suture grasping device which is capable of securely snaring a length of suture and thereafter allowing limited movement of the suture relative to the device.

Yet another object of the present invention is to provide a suture grasping device which is adapted to pierce soft tissue prior to grasping a length of suture on the far side of the tissue, whereby the suture may be passed through the soft tissue as the suture grasping device is pulled back through the soft tissue.

SUMMARY OF THE INVENTION

These and other objects of the invention are addressed by a suture grasping device which comprises a rigid, hollow shaft, a rod, a first elongate wire-like element, a second elongate wire-like element, and an actuation device.

More particularly, the rigid, hollow shaft includes a proximal end, a proximal portion adjacent to the proximal end, a pointed distal end, a distal portion adjacent to the distal end, and a lumen extending between the proximal end and the distal end. In a preferred embodiment of the invention, the inner and outer diameters of the proximal portion of the shaft are larger than the inner and outer diameters of the distal portion of the shaft. In accordance with one preferred embodiment of the invention, the distal portion of the shaft is curved.

The rod is a solid element having a proximal end and a distal end. The-rod is telescopically located in the proximal portion of the shaft. More specifically, the rod has a longitudinal length slightly greater than the longitudinal length of the proximal portion of the shaft. Accordingly, the rod may be moved between (i) a proximalmost position wherein the distal end of the rod is spaced proximally from the point where the proximal and distal portions of the shaft meet; and (ii) a distalmost position wherein the distal end of the rod is substantially aligned with the point where the proximal and distal portions of the shaft meet.

The first and second wire-like elements each have a proximal end and a distal end. The proximal ends of these wire-like elements are attached to the distal end of the rod, whereby the wire-like elements will move in conjunction with the rod. In addition, at least the distal portions of the respective wire-like elements normally bend or flare away from each other. Furthermore, the first wire-like element is bent radially inwardly immediately adjacent to its distal end so as to form a substantially hook-shaped configuration.

The longitudinal lengths of the first and second wire-like elements are selected such that when the rod is in its proximalmost position, the distal ends of the first and second wire-like elements will be located within the distal portion of the shaft. In this position, the distal ends of the first and second wire-like elements will be disposed in closely spaced relation to one another. When the rod is in its distalmost position, however, the distal ends of the first and second wire-like elements will project out the distal end of the shaft.

In this position, the distal ends of the first and-second wire-like elements will curve outwardly away from one another.

The actuation means is attached to the proximal end of the shaft and to the proximal end of the rod. In the preferred embodiment, the actuation means includes a housing attached to the proximal end of the shaft. The housing defines a cylindrical cavity which is aligned with, and opens axially into, the lumen of the shaft. A trigger is pivotally attached to the housing and extends into the cylindrical cavity. A piston is attached to the proximal end of the rod and located in reciprocally sliding relation within the housing's cylindrical cavity. A spring biases the piston proximally so that the rod will normally assume its aforementioned proximalmost position. The piston may be moved distally against the force of the spring by the trigger, so that the rod will assume its aforementioned distalmost position.

It will, therefore, be understood that the rod normally resides in its proximalmost position and the distal ends of the two wire-like elements normally reside within the distal portion of the shaft. It is to be appreciated that when the distal ends of the two wire-like elements reside within the distal portion of the shaft, the pointed distal end of the shaft may be forced through soft tissue without interference from the distal ends of the wire-like elements.

The device may be used to grasp a piece of suture at a surgical site. Among other things, it may also be used to grasp a piece of suture on the far side of a piece of soft tissue and to pass,that suture back through the soft tissue.

More particularly, in this case, the pointed distal end of the device is first forced through the soft tissue. Then the distal end of the device is manuevered so as to bring the distal end of the device up to a portion of the suture which is to be carried back through the soft tissue. Next, the trigger is activated so as to move the rod toward its distalmost position. This pushes the distal ends of the wires out the distal end of the shaft so that they flare away from each other. The tool may then be manipulated further as needed so that the distal ends of the first and second wire like elements pass on either side of a length of the target suture. It is to be appreciated that as any such further manipulation occurs, the flaring ends of the two wire-like elements will form a natural trap for enveloping the length of target suture.

The trigger is then released so as to allow the rod to return to its rearwardmost position. As this occurs, the distal ends of the wire-like elements will retreat back into the distal, portion of the shaft, with the wire-like elements moving back toward one another as they reenter the distal portion of the shaft. At the same time, as the hook at the distal end of the first wire-like element passes by the target suture, it will grapple the length of suture and carry it back toward the distal end of the shaft. As the hook at the end of the first wire-like element enters the distal end of the shaft, part of the length of suture will also be carried into the distal end of the shaft and be held there by the hook acting in cooperation with the distal end of the shaft. The hook and the shaft may be sized so that the length of suture is tightly bound to the shaft or, more preferably, the suture will be free to slide somewhat around the hook while it is inside the shaft. The distal end of the shaft may then be withdrawn from the pierced tissue, carrying the grappled suture with it so as to pass the suture through the soft tissue.

Thereafter, the length of suture may be released from the device by squeezing the trigger again, so that the two wire-like elements project back out the distal end of the shaft, thereby allowing the length of suture to separate from the tool.

BRIEF DESCRIPTION OF THE DRAWINGS

These and other objects and features of the present invention will be more fully disclosed or rendered obvious by the following detailed description of the preferred embodiment thereof, which is to be considered together with the accompanying drawings wherein like numbers refer to like parts, and further wherein.

DETAILED DESCRIPTION OF THE PREFERRED EMBODIMENT

Figure 1:
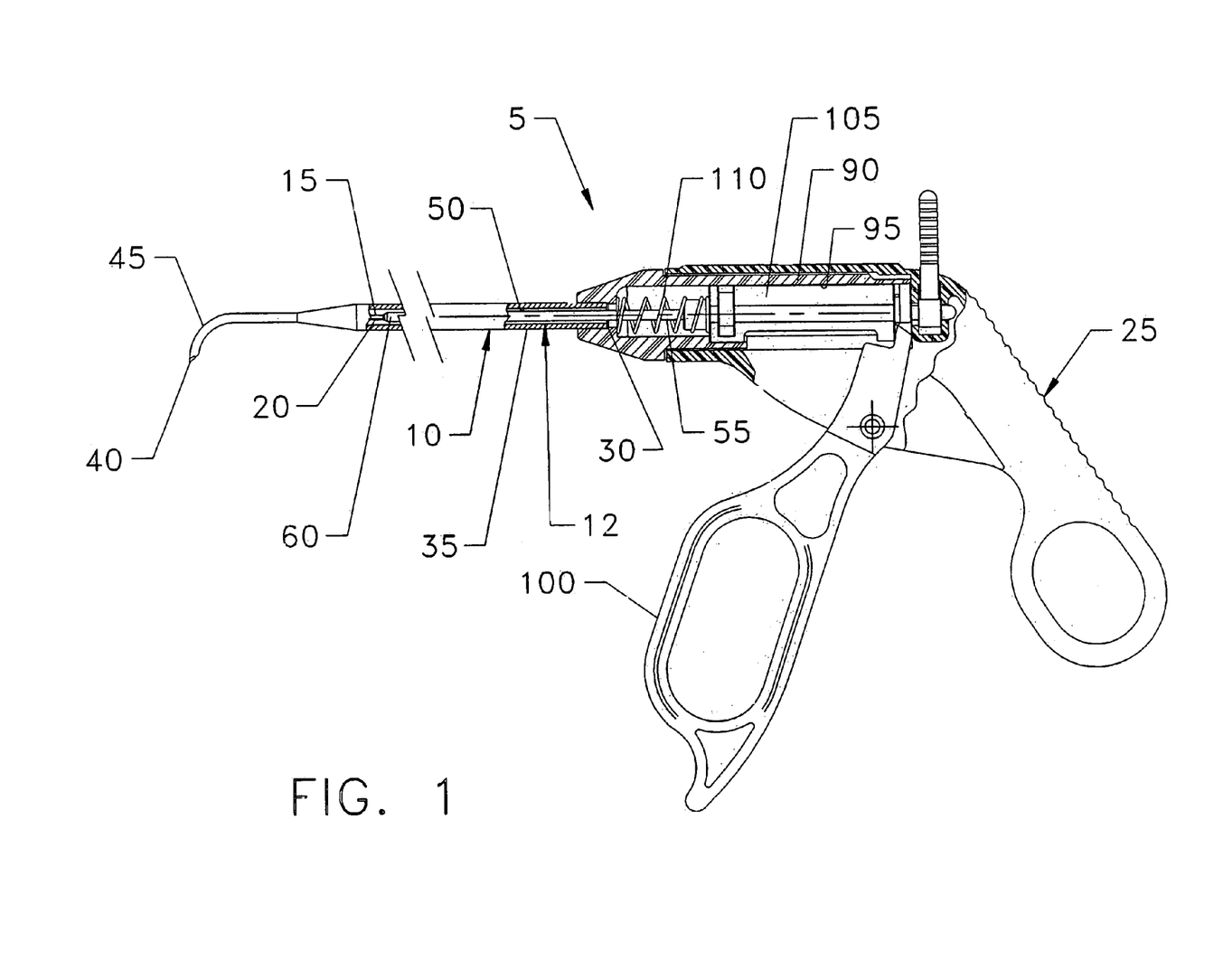
FIG. 1 is a side elevational view, partially cut away and partially in section, of a suture grasping tool formed in accordance with the present invention, wherein the rod is shown in its aforementioned proximalmost position.
Figure 2:
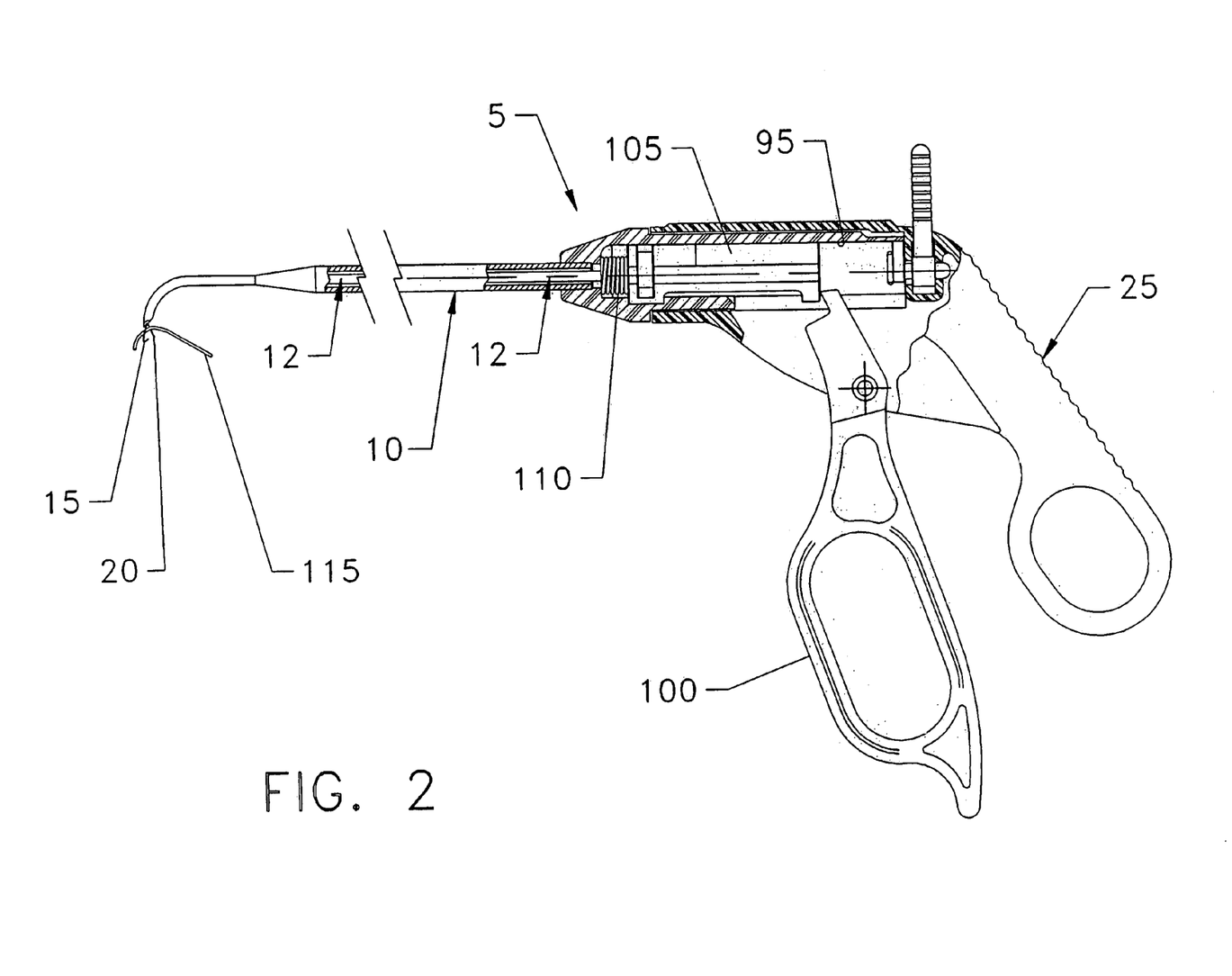
FIG. 2 is a side elevational view, partially cut away and partially in section, showing the same tool, except that the rod is shown in its aforementioned distalmost position.

Referring now to the drawings, and particularly to FIGS. 1 and 2, suture grasping tool 5 is shown which comprises a rigid, hollow shaft 10, a rod 12, a first elongate wire-like element 15, a second elongate wirelike element 20, and an actuation means 25.

More particularly, the rigid, hollow shaft 10 includes a proximal end 30, a proximal portion 35 adjacent to proximal end 30, a pointed distal end 40, a distal portion 45 adjacent to the distal end, and a lumen 50 extending between proximal end 30 and distal end 40. In a preferred embodiment of the invention, the inner and outer diameters of the proximal portion 35 of shaft 10 are larger than the inner and outer diameters of the distal portion 45 of the shaft. In accordance with one preferred embodiment of the invention, the distal portion 45 of shaft 10 is curved. Of course, it should also be appreciated that the distal portion 45 of the shaft could be formed straight if preferred.

Rod 12 is a solid element having a proximal end 55 and a distal end 60. Rod 12 is telescopically located in the proximal portion 35 of shaft 10. More specifically, rod 12 has a longitudinal length slightly greater than the longitudinal length of the proximal portion 35 of the shaft. Accordingly, rod 12 may be moved between (i) a proximalmost position wherein distal end 60 of rod 12 is spaced proximally from the point where the proximal and distal portions 35, 45 of the shaft meet (see FIG. 1); and (ii) a distalmost position wherein distaled 60 of rod 12 is substantially aligned with the point where the proximal and distal portions of the shaft meet (see FIG. 2)

Figure 3:
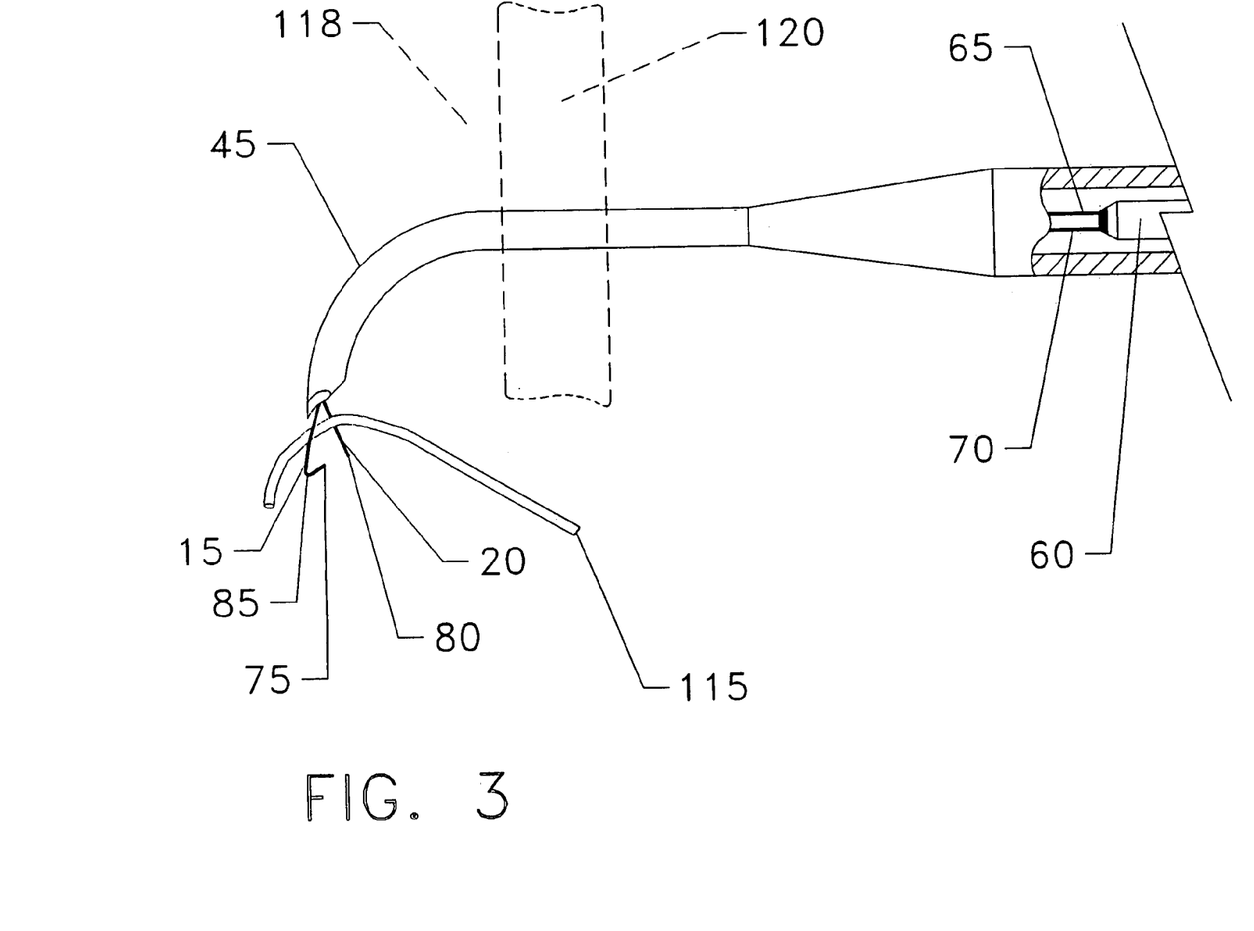
FIG. 3 is an illustrative side elevational view, partially cut away and partially in section, showing the rod in its distalmost position and the wire-like elements located on opposite sides of a piece of suture or similar material.

First and second wirelike elements 15 and 20 each have a proximal end 65, 70 and a distal end 75, 80, respectively (see FIG. 3) . Proximal ends 65 and 70 of these wirelike elements are attached to distal end 60 (FIG. 1) of rod 12, whereby the wire-like elements 15 and 20 will move in conjunction with rod 12. In addition, at least the distal ends 75 and 80 of the respective wire-like elements 15 and 20 are biased to bend or flare away from each other. Furthermore, the first wirelike element 15 is bent radially inwardly immediately adjacent to its distal end 75 so as to form a substantially hook-shaped configuration, generally indicated at 85 (FIG. 3).

The longitudinal lengths of first and second wire-like elements 15, 20 are selected such that when rod 12 is in its proximalmost position (FIG. 1), distal ends 75 and 80 of first and second wire-like elements 15 and 20 will be located within distal portion 45 of shaft 10. In this position, distal ends 75 and 80 of first and second wire-like elements 15 and 20 will be disposed in closely spaced relation to one another. When rod 12 is in its distalmost position (FIG. 2), however, distal ends 75 and 80 of first and second wire-like elements 15 and 20 will project out distal end 40 of shaft 10. In this position, distal ends 75 and 80 of first and second wire-like elements 15 and 20 will curve outwardly away from one another (FIG. 3).

Actuation means 25 (FIGS. 1 and 2) is attached to proximal end 30 of shaft 10 and to proximal end 55 of rod 12. In the preferred embodiment, actuation means 25 includes a housing 90 attached to proximal end 30 of shaft 10. Housing 90 defines a cylindrical cavity 95 which is aligned with, and opens axially into, lumen 50 of shaft 10. A trigger 100 is pivotally attached to the housing and extends into the cylindrical cavity. A piston 105 is attached to proximal end 55 of rod 12 and located in reciprocally sliding relation within the housing's cylindrical cavity 95. A spring 110 biases piston 105 proximally so that rod 12 will normally assume its aforementioned proximalmost position (FIG. 1). Piston 105 may be moved distally against the force of spring 110 by trigger 100, so that rod 12 will assume its aforementioned distalmost position (FIG. 2).

It will, therefore, be understood that rod 12 normally resides in its proximalmost position (FIG. 1) and distal ends 75 and 80 of the two wire-like elements 15 and 20 normally reside within distal portion 45 of shaft 10. It is to be appreciated that when distal ends 75 and 80 of the two wire-like elements 15 and 20 reside within distal portion 45 of shaft 10, the pointed distal end 40 of shaft 10 may be forced through soft tissue without interference from distal ends 75 and 80 of wire-like elements 15 and 20.

Figure 4:
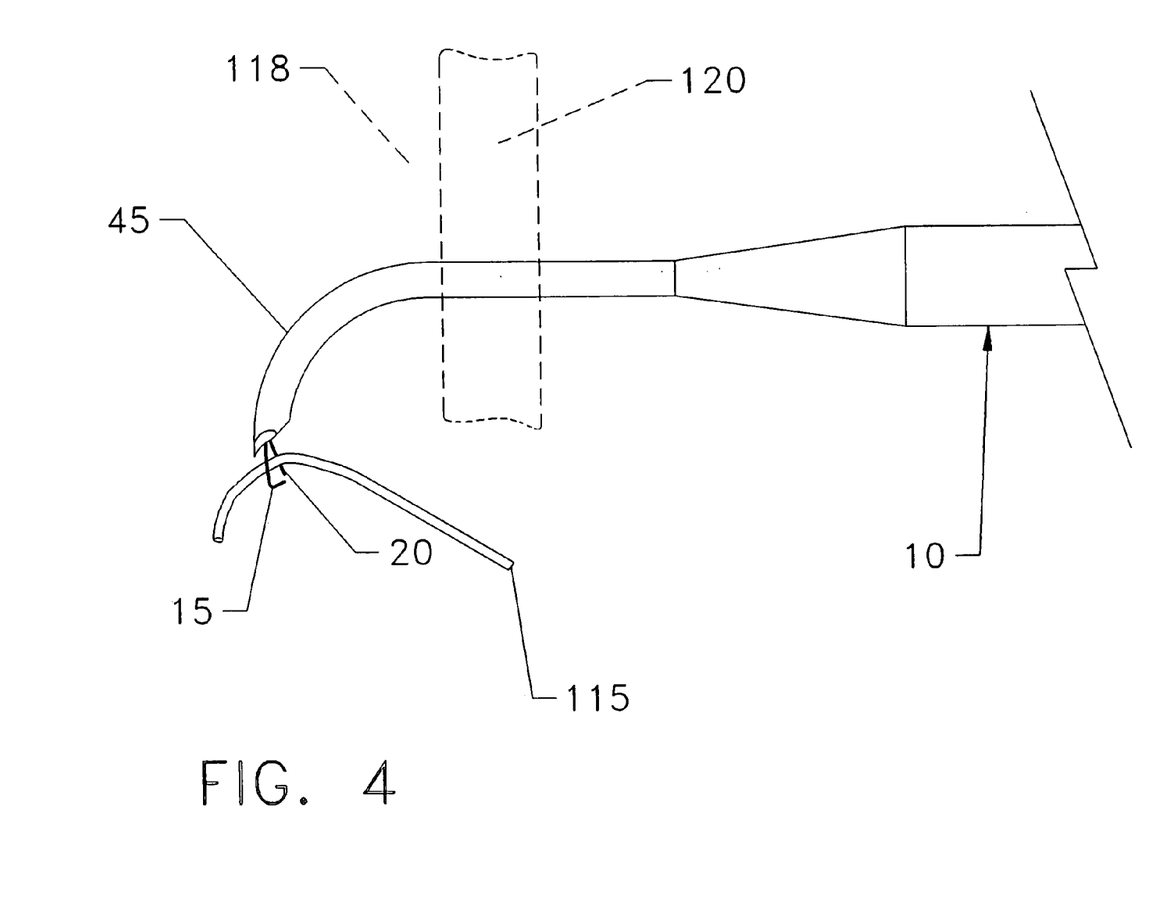
FIG. 4 is an illustrative side elevational view of the shaft showing the wire-like elements partially withdrawn into the distal portion of the shaft and substantially surrounding a piece of suture.

Tool 5 may be used to grasp a piece of suture 115 at a surgical site (FIGS. 3 and 4). Among other things, it may also be used to grasp a piece of suture 115 on the far side 118 of a piece of soft tissue 120 and to pass that suture back through the soft tissue.

More particularly, in this case, pointed distal end 40 of tool 5 is first forced through soft tissue 120. Then distal end 40 of tool 5 is maneuvered so as to bring the distal end up to a portion of the suture 115 which is to be carried back through soft tissue 120. Next, trigger 100 is activated so as to move rod 12 toward its distalmost position. This pushes distal ends 75 and 80 of wires 15 and 20 out distal end 40 of shaft 10 50 that they flare away from each other (FIG. 3). Tool 5 may then be manipulated further as needed so that distal ends 75 and 80 of first and second wirelike elements 15 and 20 pass on either side of a length of target suture 115. It is to be appreciated that as any such further manipulation occurs, the flaring ends of the two wire-like elements 15 and 20 will form a natural trap for enveloping the length of target suture 115.

Figure 5:
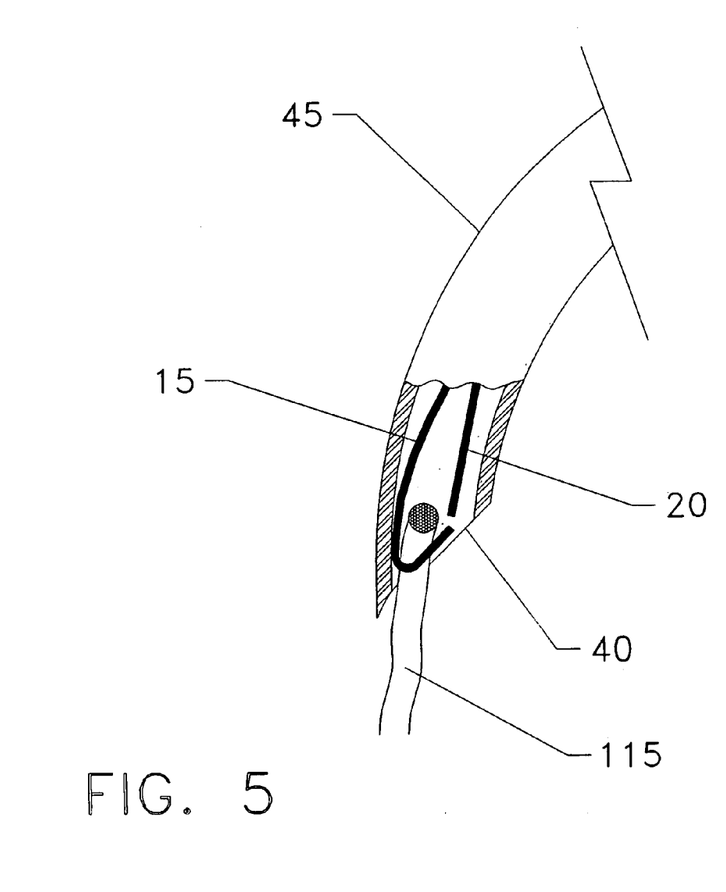
FIG. 5 is an illustrative side elevational view, partially in section, of the distal portion of the shaft, showing the wire-like elements withdrawn to their proximalmost position within the shaft and grasping a length of suture to the tool.

Trigger 100 is then released so as to allow rod 12 to return to its rearwardmost position. As this occurs, distal ends 75 and 80 of the wire-like elements will retreat back into distal portion 45 of shaft 10, with wire-like elements 15 and 20 moving back toward one another as they reenter distal portion 45 of shaft 10 (see FIG. 4). At the same time, as the hook 85 at the distal end of the first wire-like element 15 passes by target suture 115, it will grapple the length of suture and carry it back toward the distal end of the shaft. As hook 85 enters the distal end of the shaft, part of the length of suture 115 will also be carried into the distal end of the shaft and be held there by hook 85 acting in cooperation with the distal end 40 of the shaft (FIG. 5). The hook and the shaft may be sized so that the length of suture is tightly bound to the shaft or, more preferably, the suture will be free to slide somewhat around the hook while it is inside the shaft. The distal end 40 of the shaft may then be withdrawn from the pierced tissue 120, carrying the grappled suture 115 with it so as to pass the suture through the soft tissue.

Thereafter, the length of suture 115 may be released from tool 5 by squeezing trigger 100 again, so that the two wire-like elements 15 and 20 project back out the distal end of the shaft, thereby allowing the length of suture to separate from the tool.

Numerous changes, alterations, variations modifications and uses of the present invention will occur to those skilled in the art, in view of the foregoing detailed description of the preferred embodiment thereof. It should therefore be understood that the foregoing specification has been presented by way of illustration and not limitation. It is intended that the present invention should be limited only by the terms of the claims appended hereto.

What is claimed is:

1. A device for grasping and carrying thin cord-like objects comprising:

a hollow, substantially rigid shaft having a proximal end, a straight proximal portion extending along an axis distally of the proximal end, a curved rigid distal portion having a curved centerline curving away from the axis, and a distal end, the distal end being pointed and adapted to pierce soft tissue, and a lumen extending along the axis and the curved centerline from the proximal end to the distal end of said shaft;

a solid rod having a proximal end and a distal end, said rod being positioned in the lumen of the proximal portion of the shaft in reciprocally sliding relationship therewith;

first and second wire-like elements, each having a distal end and a proximal end, said first and second wire-like elements being attached at their respective proximal ends to the distal end of said rod so as to extend distally therefrom and move through the curved distal portion of the shaft in conjunction with the movement of said rod along the axis, said first wire-like element defining a hook-shaped configuration at the distal end thereof; and actuation means attached to the proximal end of said rod and to the proximal end of said shaft for moving said rod and said wire-like elements between: (i) a first position wherein the distal ends of said wire-like elements are contained within said shaft in closely spaced relation to one another, and (ii) a second position wherein the distal ends of said wire-like elements extend outwardly from the distal end of said shaft in flared relationship to one another, wherein said actuation means comprises:

a housing attached to the proximal end of said shaft;

a trigger pivotally attached to said housing; and a spring biased piston attached to the proximal end of said rod and configured to slide within said housing so as to move said rod between the first and second positions;

said first and second wire-like elements being adapted so that when said wire-like elements are in the second position, the distal ends of said first wire-like element and said second wire-like element cooperate to define a gap therebetween for receiving and trapping the thin cord-like object, and wherein the distal end of said first wire-like element grasps the thin cord-like object and carries the thin cord-like object back toward and into the distal end of said shaft when said wire-like elements are moved from the second position to the first position;

whereby said wire-like elements are further adapted to secure the thin cord-like object to said shaft when said wire-like elements are moved from the second position to the first position and release the thin cord-like object when said wire-like elements are moved from the first position to the second position.

2. A method for grasping and carrying a thin cord-like object comprising:

(1) providing a device comprising:

a hollow, substantially rigid shaft having a proximal end, a straight proximal portion extending along an axis distally of the proximal end, a curved rigid distal portion having a curved centerline curving away from the axis and a distal end, the distal end being pointed and adapted to pierce soft tissue, and a lumen extending along the axis and the curved centerline from the proximal end to the distal end of said shaft;

a solid rod having a proximal end and a distal end, said rod being positioned in the lumen of the proximal portion of the shaft in reciprocally sliding relationship therewith;

first and second wire-like elements each having a distal end and a proximal end, said first and second wire-like elements being attached at their respective proximal ends to the distal end of said rod so as to extend distally therefrom and move through the curved distal portion of the shaft in conjunction with the movement of said rod, said first wire-like element defining a hook-shaped configuration at the distal end thereof; and actuation means attached to the proximal end of said rod and to the proximal end of said shaft for moving said rod and said wire-like elements between (i) a first position wherein the distal ends of said wire-like elements are contained within said shaft in closely spaced relation to another, and (ii) a second position wherein the distal ends of said wire-like elements extend outwardly from the distal end of said shaft in flared relationship to one another, wherein the actuation means comprises:

a housing attached to the proximal end of said shaft;

a trigger pivotally attached to said housing; and a spring biased piston attached to the proximal end of said rod and configured to slide within said housing so as to move said rod between the first and second positions;

(2) positioning said rod and said wire-like elements in the first position;

(3) forcing the distal end of said shaft through the soft tissue and maneuvering the distal end of said shaft so that it is adjacent to the thin cord-like object which is to be grasped;

(4) positioning said rod and said wire-like elements in the second position by activating said trigger of the actuation means, and maneuvering the distal end of said shaft as needed so as to position the flared distal ends of said wire-like elements on opposite sides of the cord-like object so as to define a gap therebetween for receiving and trapping the thin cord-like object;

(5) thereafter positioning said rod and said wire-like elements in the first position by releasing the trigger of the actuation means, whereby the distal end of said first wire-like element grasps the thin cord-like object and carries the thin cord-like object back toward and into the distal end of said shaft as said wire-like elements are moved from the second position to the first position, whereby the wire-like elements are adapted to secure the thin cord-like object to said shaft when said wire-like elements are moved from the second position to the first position and release the thin cord-like object when said wire-like elements are moved from the first position to the second position; and (6) repeating steps (2) through (5) so as to further maneuver the distal end of said shaft to grasp the thin cord-like object and pass it through the soft tissue.

* * * * *